US005849516A

United States Patent [19]

Wu et al.

[11] Patent Number: 5,849,516

[45] Date of Patent: Dec. 15, 1998

[54] SEMISELECTIVE MEDIUM COMPOSITION FOR DETECTING SEED-BORNE *ALTERNARIA BRASSICICOLA*

[75] Inventors: Wen-Shi Wu; Tse-Wei Chen, both of Taipei, Taiwan

[73] Assignee: National Science Council, Taipei, Taiwan

[21] Appl. No.: 914,836

[22] Filed: Aug. 19, 1997

[30] Foreign Application Priority Data

Aug. 4, 1997 [TW] Taiwan ................................ 86111143

[51] Int. Cl.$^6$ ................................ C12Q 1/04; C12N 1/14

[52] U.S. Cl. .......................... 435/34; 435/256.8; 435/431

[58] Field of Search ................................ 435/256.8, 431, 435/34

[56] References Cited

U.S. PATENT DOCUMENTS

| | | | |
|---|---|---|---|
| 4,375,510 | 3/1983 | Jordan | 435/34 |
| 5,573,947 | 11/1996 | Madec et al. | 435/253.6 |

OTHER PUBLICATIONS

Wu et al. in *Plant Protection Bulletin* 26:67–72 (1984) "A Semiselective Medium for Detecting Seed–borne *Alternaria brassicicola*".
Wu et al. Plant Protection Bulletin 26:67–72, 1984.
Huang et al. Plant Protection Bulletin 24: 364, 1981.

*Primary Examiner*—Gary L. Kunz
*Attorney, Agent, or Firm*—Ladas & Parry

[57] ABSTRACT

The present invention provides a novel semiselective medium composition for detecting seed-borne *Alternaria brassicicola*, which comprises galactose, calcium nitrate, dipotassium hydrogen phosphate, magnesium sulfate, agar, benomyl, and chloramphenicol. The CW medium of the present invention can selectively allow seed-borne *Alternaria brassicicola* to grow, while effectively suppressing the growth of other seed-borne fungi. Although *A. alternata*, which is prevalently present on seeds and is similar to *A. brassicicola*, can still grow on the CW medium, the color of the *A. alternata* colonies are different from that of *A. brassicicola*, thus, *A. brassicicola* can be obviously differentiated.

20 Claims, No Drawings

SEMISELECTIVE MEDIUM COMPOSITION FOR DETECTING SEED-BORNE *ALTERNARIA BRASSICICOLA*

BACKGROUND OF THE INVENTION

1. Field of the Invention

The present invention relates to a semiselective medium composition (CW medium) for detecting seed-borne *Alternaria brassicicola* and a process for detecting the same, and more particularly relates to a semiselective medium composition containing galactose and calcium nitrate. *Alternaria brassicicola* can grow on the CW medium and can be readily differentiated from *Alternaria alternata* based on the color.

2. Description of the Prior Art

Black leaf spot of cruciferous crops caused by *Alternaria brassicicola* is a very important seed-transmitted (seed-borne) disease. Such a seed-borne pathogen not only decreases the percentage of seedling emergence, but also infects the growing plants. It is known that the percentage of the seeds carrying pathogens is positively correlated with the percentage of the germinated seeds and the percentage of the diseased seedlings. Therefore, there is a need to provide a process for detecting the pathogen *Alternaria brassicicola* on or in seeds.

To date, the process for detecting *Alternaria brassicicola* on or in seeds still has some disadvantages. For example, conventionally, the blotter method or deep freezing blotter method have been provided to detect a seed-borne pathogen. However, by these two methods, several different species of microorganisms on the seed can grow; and the pathogen to be detected is usually covered by the quickly growing fungi. Therefore, operators cannot identify the real pathogen to be detected, thus wasting time and adversely affecting the accuracy of detection.

To overcome the disadvantage of the blotter method and the deep freezing blotter method, researchers have provided a semiselective medium to detect *Alternaria brassicicola*. For example, Wu et al. in *Plant Protection Bulletin* 26:67–72 (1984) provide a semiselective medium for detecting *Alternaria brassicicola*, which includes 20 g of agar, 1 g of potassium dihydrogen phosphate ($KH_2PO_4$), 0.5 g of magnesium sulfate ($MgSO_4.7H_2O$), 5 g of peptone, 10 g of dextrose, 0.5 g of sodium propionate, 100 ppm of benomyl, 100 ppm of streptomycin sulfate, and 1 liter of distilled water.

In addition, Huang et al. on page 279 in the thesis abstract of the 1981 annual meeting of the Chinese Plant Protection Society; provide another semiselective medium for detecting *Alternaria brassicicola*, which includes 20 g of sucrose, 3 g of ammonium sulfate, 20 g of agar, 3 g of potassium dihydrogen phosphate ($KH_2PO_4$), 0.5 g of magnesium sulfate ($MgSO_4.7H_2O$), 15 g of peptone, 20 ppm of neomycin, 50 ppm of chloramphenicol, 50 ppm of A-40 (Dithane A-40), 50 ppm of benomyl, and 1 liter of distilled water.

However, to date, the conventional semiselective medium for detecting *Alternaria brassicicola* cannot distinguish *A. brassicicola* from *Alternaria alternata*, which is prevalently present in various seeds. In addition, if the *A. brassicicola* infected (-diseased) seeds are placed on such semiselective medium, since the microorganisms growing on the medium are very complex, and since the morphology and size of the spores of *A. alternata* and *A. brassicicola* are very similar, *A. brassicicola* can not be differentiated on such a medium. Because of these disadvantages, the medium needs to be improved.

Since *Alternaria brassicicola* can survive not only on the surface of seeds, but also inside the seeds in the form of mycelia, *A. brassicicola* on or in the seeds must be accurately detected by a medium method.

SUMMARY OF THE INVENTION

Thus, the object of the present invention is to provide a sensitive semiselective medium, which can be utilized to detect seed-borne *Alternaria brassicicola* quickly and accurately.

To achieve the above-mentioned object, the semiselective medium composition for detecting *Alternaria brassicicola* comprises galactose, calcium nitrate, dipotassium hydrogen phosphate, magnesium sulfate, agar, benomyl, and chloramphenicol. The novel medium of the present invention is called CW medium, based on the initials of the family names of the inventors of the present invention, Chen and Wu.

DETAILED DESCRIPTION OF THE INVENTION

According to the present invention, the CW medium can selectively allow *Alternaria brassicicola* to grow, while effectively suppressing the growth of some common saprophytic seed-borne fungi, i.e., Aspergillus spp., Cladosporium spp., Fusarium spp., Penicillium spp., and Ulocladium spp.

*Alternaria alternata* is prevalently present on various seeds, and the morphology and size of the spores of *A. alternata* are very similar to that of *A. brassicicola*. When the *A. brassicicola*-infected seeds are placed on a conventional semiselective medium, since the microorganisms growing on the medium are very complicated, *A. brassicicola* cannot be differentiated from the colonies on the medium.

However, the novel semiselective medium developed by the present invention can thus solve the above-mentioned problems. Although *A. alternata* can still grow on the semiselective medium of the present invention, it is obvious that the colonies of *A. alternata* are white, while the colonies of *A. brassicicola* are darkish brown to black. In addition, the CW medium of the present invention can effectively suppress the growth of other seed-borne fungi, thus the growing microorganisms are much simpler. Therefore, by using the CW medium of the present invention, one can determine accurately whether a seed to be tested has been infected by *A. brassicicola* or not; and false detection caused by the *A. alternata* interference can be prevented.

The semiselective medium composition of the present invention includes: galactose, calcium nitrate [$Ca(NO_3)_2.4H_2O$], dipotassium hydrogen phosphate ($K_2HPO_4$), magnesium sulfate ($MgSO_4.7H_2O$), agar, benomyl, and chloramphenicol.

The concentration of each component in the semiselective medium of the present invention can be varied according to practical needs, and thus should not be strictly limited. Generally speaking, in one liter of the medium, preferably, the semiselective medium contains 10–60 g of galactose, 1–5 g of calcium nitrate, 0.5–1.5 g of dipotassium hydrogen phosphate, 0.5–1.5 g of magnesium sulfate, 15–30 g of agar, 50–150 ppm of benomyl, and 50–150 ppm of chloramphenicol.

The present invention further provides a method for detecting seed-borne *Alternaria brassicicola*. First, the CW semiselective medium composition as mentioned above is provided. Then, a biological sample is placed on the semiselective medium. The biological sample is incubated to make seed-borne *Alternaria brassicicola* and other microorganisms grow on the semiselective medium. Finally, the seed-borne *Alternaria brassicicola* on the semiselective medium is detected.

Since *Alternaria brassicicola* is transmitted long distance by seeds, and is often present on the surface or inside the infected seeds, generally speaking, the detection method of the present invention is particularly suitable for applying to test a seed, but is not limited to this. All biological samples other than seeds are also suitable. Moreover, since *Alternaria brassicicola* readily infects cruciferous crops, the detection method of the present invention is particularly suitable for detecting *Alternaria brassicicola* on or in seeds of cruciferous crops.

The following example is intended to illustrate the process and the advantages of the present invention more fully without limiting its scope, since numerous modifications and variations will be apparent to those skilled in the art.

EXAMPLE

The components of CW medium include two parts: part (A) and part (B). Part (A) contains 30 g of galactose, 3 g of calcium nitrate, 1 g of dipotassium hydrogen phosphate, 1 g of magnesium sulfate, and 20 g of agar. Part (B) contains 100 ppm of benomyl and 100 ppm of chloramphenicol.

The components of part (A) were added to and dissolved in a liter of distilled water. The solution was sterilized by autoclaving for 15 minutes. After the solution was cooled to 50° C., the reagents of part (B) were added. After part (A) and part (B) were thoroughly mixed, the CW medium obtained was poured into sterile Petri dishes (having a diameter of 9 cm) to make plates, 15 mL of CW medium per dish. After the plates were cooled, 25 seeds were evenly placed on a plate. The dishes were incubated at 24° C. with diurnal light (2200 lux, 12 hours) for 7 days. The color and morphology of the colonies on the plates are observed by the naked eye or by a stereo-microscope.

On the CW medium, the colonies of *Alternaria brassicicola* are darkish brown to black color with black powdery fruiting structures; thus, these characteristics can be used to identify the colonies of *A. brassicicola*, regardless the size of the colony. Although *A. alternata* can still grow on the CW medium, the colonies are white, which can be easily differentiated from the colonies of *A. brassicicola*. Therefore, those skilled in the art can easily identify the colonies of *A. brassicicola* on the CW medium directly by the naked eye, according to the morphology and characteristics of *A. brassicicola*. The observation time for detecting *A. brassicicola* on the CW medium is much shorter than that for detecting *A. brassicicola* by the blotter method or the deep freezing blotter method. Thus, for operators and researchers who must test a large number of seeds, the testing time can be drastically reduced. In addition, the method for detecting *A. brassicicola* by the CW medium of the present invention is much more sensitive than other conventional methods.

What is claimed is:

1. A semiselective medium composition for detecting seed-borne *Alternaria brassicicola*, comprising:

galactose, calcium nitrate, dipotassium hydrogen phosphate, magnesium sulfate, agar, benomyl, and chloramphenicol.

2. The semiselective medium composition as claimed in claim 1, comprising:

10–60 g of galactose,

1–5 g of calcium nitrate, 0.5–1.5 g of dipotassium hydrogen phosphate, 0.5–1.5 g of magnesium sulfate, 15–30 g of agar, 50–150 ppm of benomyl, and 50–150 ppm of chloramphenicol, per liter of the medium composition.

3. The semiselective medium composition as claimed in claim 2, comprising:

30 g of galactose, 3 g of calcium nitrate, 1 g of dipotassium hydrogen phosphate, 1 g of magnesium sulfate, 20 g of agar, 100 ppm of benomyl, and 100 ppm of chloramphenicol, per liter of the medium composition.

4. A method for detecting seed-borne *Alternaria brassicicola*, comprising:

(a) providing the semiselective medium composition as claimed in claim 1;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by morphology of the *Alternaria brassicicola.*

5. The process as claimed in claim 4, wherein the biological sample is a seed.

6. The process as claimed in claim 5, wherein the seed is a seed of cruciferous crops.

7. A method for detecting seed-borne *Alternaria brassicicola*, comprising:

(a) providing the semiselective medium composition as claimed in claim 1;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by color.

8. A method as claimed in claim 7, wherein the *Alternaria brassicicola* in step (d) is brown to black in color.

9. A method for detecting seed-borne *Alternaria brassicicola*, comprising:

(a) providing the semiselective medium composition as claimed in claim 1;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by the presence of black powdery fruiting structures.

10. A method for detecting seed-borne *Alternaria brassicicola*, comprising:

(a) providing the semiselective medium composition as claimed in claim 1;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium, wherein the *Alternaria brassicicola* in step (d) comprises colonies having a brown to black color with black powdery fruiting structures.

11. A method for detecting seed-borne *Alternaria brassicicola*, comprising:

(a) providing the semiselective medium composition as claimed in claim 2;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by morphology of the *Alternaria brassicicola.*

12. A method for detecting seed-borne *Alternaria brassicicola*, comprising:

(a) providing the semiselective medium composition as claimed in claim 2;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by color.

13. A method as claimed in claim 12, wherein the *Alternaria brassicicola* in step (d) is brown to black in color.

14. A method for detecting seed-borne *Alternaria brassicicola*, comprising:

(a) providing the semiselective medium composition as claimed in claim 2;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by the presence of black powdery fruiting structures.

15. A method for detecting seed-borne *Alternaria brassicicola*, comprising:

(a) providing the semiselective medium composition as claimed in claim 2;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium, wherein the *Alternaria brassicicola* in step (d) comprises colonies having a brown to black color with black powdery fruiting structures.

16. A method for detecting seed-borne *Alternaria brassicicola*, comprising:

(a) providing the semiselective medium composition as claimed in claim 3;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by morphology of the *Alternaria brassicicola.*

17. A method for detecting seed-borne *Alternaria brassicicola*, comprising:

(a) providing the semiselective medium composition as claimed in claim 3;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by color.

18. A method as claimed in claim 17, wherein the *Alternaria brassicicola* in step (d) is brown to black in color.

19. A method for detecting seed-borne *Alternaria brassicicola*, comprising:

(a) providing the semiselective medium composition as claimed in claim 3;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium by the presence of black powdery fruiting structures.

20. A method for detecting seed-borne *Alternaria brassicicola*, comprising:

(a) providing the semiselective medium composition as claimed in claim 3;

(b) placing a biological sample on the semiselective medium;

(c) incubating the biological sample and allowing seed-borne *Alternaria brassicicola* and other microorganisms to grow on the semiselective medium; and (d) detecting seed-borne *Alternaria brassicicola* on the semiselective medium, wherein the *Alternaria brassicicola* in step (d) comprises colonies having a brown to black color with black powdery fruiting structures.

* * * * *